US006674834B1

(12) United States Patent
Acharya et al.

(10) Patent No.: US 6,674,834 B1
(45) Date of Patent: Jan. 6, 2004

(54) PHANTOM AND METHOD FOR EVALUATING CALCIUM SCORING

(75) Inventors: Kishore C. Acharya, Brookfield, WI (US); Thad A. Heinold, Delafield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/541,157

(22) Filed: Mar. 31, 2000

(51) Int. Cl.[7] .............................................. A61B 6/00
(52) U.S. Cl. .................................. 378/18; 378/207
(58) Field of Search ................................ 378/18, 207

(56) References Cited

U.S. PATENT DOCUMENTS

| | | | |
|---|---|---|---|
| 4,182,311 A | | 1/1980 | Seppi et al. |
| 4,352,020 A | * | 9/1982 | Horiba et al. ................ 378/18 |
| 4,646,334 A | * | 2/1987 | Zerhouni ..................... 378/18 |
| 4,837,686 A | | 6/1989 | Sones et al. |
| 4,870,666 A | | 9/1989 | Lonn |
| 4,873,707 A | * | 10/1989 | Robertson .................... 378/18 |
| 4,985,906 A | | 1/1991 | Arnold |
| 5,034,969 A | * | 7/1991 | Ozaki .......................... 378/18 |
| 5,335,260 A | | 8/1994 | Arnold |
| 6,154,516 A | | 11/2000 | Heuscher et al. |
| 6,224,257 B1 | * | 5/2001 | Launay et al. ............. 250/252.1 |
| 6,233,304 B1 | | 5/2001 | Hu et al. |
| 6,314,313 B1 | * | 11/2001 | Romeas et al. .............. 378/18 |
| 6,421,552 B1 | | 7/2002 | Hsieh |

FOREIGN PATENT DOCUMENTS

| | | |
|---|---|---|
| EP | 1 016 376 A2 | 7/2000 |
| EP | 1 092 392 A2 | 4/2001 |
| WO | WO 00/33252 | 6/2000 |

OTHER PUBLICATIONS

Lynn S. Broderick et al.; "Measurement of Coronary Artery Calcium with Dual–Slice Helical CT Compared with Coronary Angiography: Evaluation of CT Scoring Methods, Interobserver Variations, and Reproducibility"; AJR:167; Aug. 1996; pp. 439–444.

Hyo–Chun Yoon, MD, PhD., et al.; "Coronary Artery Calcium: Alternate Methods for Accurate and Reproducible Quantitation"; AUR; Oct. 1997; vol. 4, No. 10; pp. 666–673.

Arthur S. Agatston, MD, FACC, et al.; "Quantification of Coronary Artery Calcium Using Ultrafast Computed Tomography"; JACC vol. 15, No. 4; Mar. 15, 1990; pp. 827–832.

Yuji Ukai et al.; "A Coronary Calcification Diagnosis System Based on Helical CT Images"; IEEE; 1998; pp. 1208–1212.

(List continued on next page.)

*Primary Examiner*—Robert H. Kim
*Assistant Examiner*—Hoon K. Song
(74) *Attorney, Agent, or Firm*—Carl B. Horton, Esq.; Armstrong Teasdale LLP

(57) ABSTRACT

A method is described for evaluating substance scoring, the scoring based on imaging system-generated images of an object having regions of interest due to possible presence of the substance, the method including the steps of simulating the regions of interest using a phantom having a plurality of volumes, each volume having dimensions simulating dimensions of a region of interest, each volume having a density representative of a substance density; generating images of the phantom; scoring the substance based on the phantom images; and comparing results of the substance scoring to expected phantom-image results. The above-described phantom and method allow a scoring system user to verify substance scoring accuracy and to compare scores resulting from different imaging systems, scanning methods and reconstruction algorithms.

14 Claims, 5 Drawing Sheets

OTHER PUBLICATIONS

Wilson et al.; "Automated Detection of Microcalcifications in Mammograms through Application of Image Pixel Remapping and Statistical Filter"; Eleventh IEEE Symposium on Computer–Based Medical Systems; pp. 270–274.

Okhashi et al.; "Application of a Neural Network to Automatic Gray–level Adjustment for Medical Images"; IEEE vol. 2 of 3; Nov. 1991; pp. 974–980.

"Catphan", 32 page (17 page as photocopied) brochure; Product of the Phantom Laboratory.*

PCI SPECIAL INTEREST GROUP, "PCI Local Bus Specification, Revision 2.2," pp. i–ii, 52–61 (Dec. 1998).

"Liquid–Phil™ Phantoms"; 8–page (4–page as photocopied) brochure; Product of *The Phantom* Laboratory.

"Magphan®"; 24–page (13–page as photocopied) brochure; Product of *The Phantom* Laboratory.

"Quantification of Coronary Artery Calcium Using Ultrafast Computed Technology"; Agatston et al.; Journal of the American College of Cardiology, vol. 15, No. 4, pp. 827–832 (Mar. 15, 1990).

"R S VP Pelvis™"; 6–page (3–page as photocopied) brochure; Product of *The Phantom* Laboratory.

"R S V P Phantom™ Radiosurgery Verification Phantom"; 8–page (4–page as photocopied) brochure; Product of *The Phantom* Laboratory.

"Sectional Phantoms"; 8–page (4–page as photocopied) brochure; Product of *The Phantom* Laboratory.

"The Phantom Patient™"; 8–page (4–page as photocopied) brochure; Product of *The Phantom* Laboratory.

"The RANDO® Phantom"; 8–page (4–page as photocopied) brochure; Product of *The Phantom* Laboratory.

"Welcome to The Phantom Laboratory"; 28–page (15–page as photocopied) brochure; Product of *The Phantom* Laboratory.

"Three–Dimensional Biomedical Imaging", Richard A. Robb, Ph.D., vol. 1 Chapter 5, pp. 139–146; CRC Press, Inc. (1985).

"Development and Assessment of Real Cardiac Motion Simulation Phantom"; Article [in Japanese]; Kimura F. et al.; Nippon Acta Radiologica; 61(1):29–32 (Jan. 2001).

"Vascular Surgery" ('Saphenous Vein Harvesting', 'Saphenous Vein Harvesting–Balloon', 'Heart Surgery'); 3–page document; [obtained from Internet www.limbsandthings.com/surgpg7.htm]; [Page last updated; Jun. 19, 2001].

"Vascular Surgery" ('Saphenous Leg for Vein Harvesting', 'Saphenous Vein Balloon Harvesting Trainer', 'Pulsatile Heart and Pump') 3–page document; [obtained from Internet www.limbsandthings.com/vascular.htm]; [Page last updated Jun. 19, 2001].

"Study of Cardiac Ejection Fraction and Volume Measurements Using a Dynamic Cardia Phantom and SPECT"; S. Jang et al.; vol. 3, pp. 1581–1585; In the Conference Record of the IEEE Nuclear Science Symposium & Medical Imaging Conference in San Francisco, CA, held Oct. 31–Nov. 6, 1993, by the IEEE.

"Evaluation of Ejection Fraction Measurements in Gated Cardiac Imaging Using Dynamic Cardia Phantoms"; S. Jang et al.; vol. 4, pp. 1735–1738; In the Conference Record of the IEEE Nuclear Science Symposium & Medical Imaging Conference in Norfolk, VA, held Oct. 30–Nov. 5, 1994, by the IEEE.

"Cardiac Ejection Fraction and Volume Measurements Using a Dynamic Cardia Phantoms Radionuclide Imaging"; S. Jang et al.; vol. 41, No. 6, pp. 2845–2849; Dec. 1994; IEEE Transactions on Nuclear Science.

* cited by examiner

| Group Number | Algorithm Range | Target CT Number at 120 KV | Group angle (in degrees) |
| --- | --- | --- | --- |
| 1 | - | 0 HU | 0 |
| 2 | 0 - 129 HU | 110 HU | 45 |
| 3 | 130 - 199 HU | 150 HU | 135 |
| 4 | 200 - 299 HU | 250 HU | 180 |
| 5 | 300 - 399 HU | 350 HU | 225 |
| 6 | 400+ HU | 450 HU | 315 |

PHANTOM AND METHOD FOR EVALUATING CALCIUM SCORING

BACKGROUND OF THE INVENTION

This invention relates generally to imaging systems and, more particularly, to a phantom for use in evaluating substance scoring using imaging system-generated images.

Imaging systems include a source that emits signals (including but not limited to x-ray, radio frequency, or sonar signals), and the signals are directed toward an object to be imaged. The emitted signals and the interposed object interact to produce a response that is received by one or more detectors. The imaging system then processes the detected response signals to generate an image of the object.

For example, in computed tomography (CT) imaging, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third-generation CT systems, the x-ray source and the detector array are rotated with a gantry within the imaging plane and around the object to be imaged so that the angle at which the x-ray beam intersects the object constantly changes. A group of x-ray attenuation measurements, i.e. projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two-dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one-fan-beam helical scan. The helix mapped out by the fan beam yields projection data from which images in each prescribed slice may be reconstructed. In addition to reduced scanning time, helical scanning provides other advantages such as improved image quality and better control of contrast.

It is known to use imaging data to identify evidence of disease by detecting and quantifying, i.e. "scoring", substances that may be present in a patient's system. One known software system, for example, analyzes CT images of the heart to quantify amounts of calcium in coronary regions of interest. Scoring is based upon the volume and Hounsfield unit of a calcified region. A number called the "calcium score" expresses the quantity of calcium present in the patient's arterial system.

It would be desirable to provide a method for verifying accuracy of substance-scoring systems. It also would be desirable to provide a method for measuring the validity, reproducibility and repeatability of a substance score for different imaging systems (e.g. CT single-slice or multi-slice), for different scanning methods (e.g. CT helical or axial), and for different image reconstruction algorithms.

BRIEF SUMMARY OF THE INVENTION

There is therefore provided, in one embodiment, a method for evaluating substance scoring, the scoring based on imaging system-generated images of an object having regions of interest due to possible presence of the substance, the method including the steps of simulating the regions of interest using a phantom having a plurality of volumes, each volume having dimensions simulating dimensions of a region of interest, each volume having a density representative of a substance density; generating images of the phantom; scoring the substance based on the phantom images; and comparing results of the substance scoring to expected phantom-image results.

The above-described phantom and method allow a scoring system user to verify substance scoring accuracy and to compare scores resulting from different imaging systems, scanning methods and reconstruction algorithms.

DETAILED DESCRIPTION OF THE INVENTION

Figure 1:
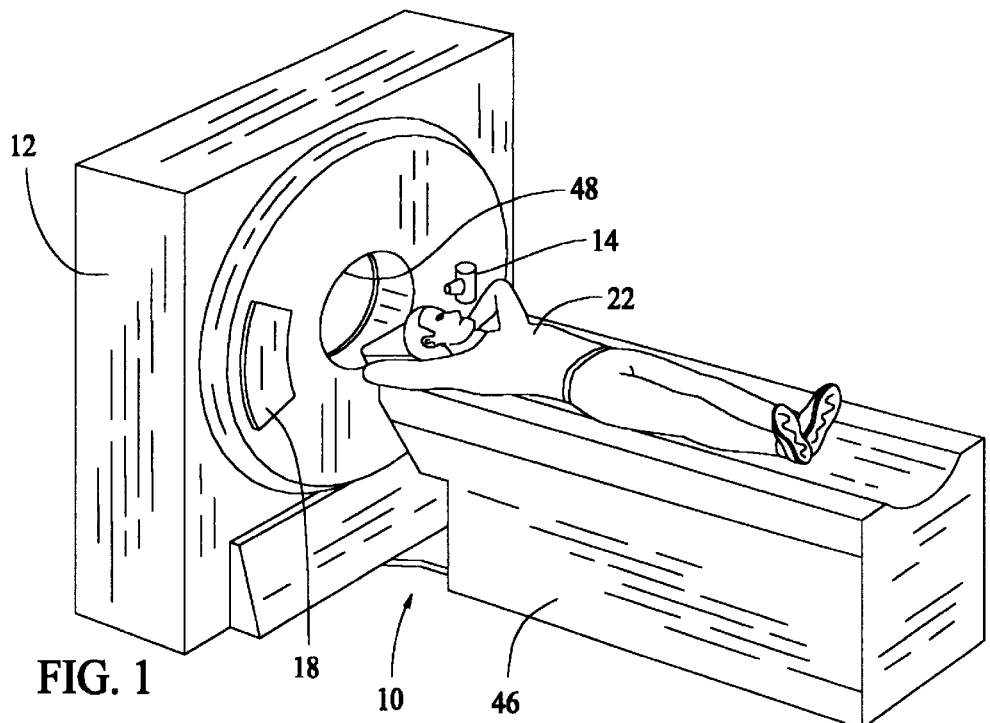
FIG. 1 is a pictorial view of a CT imaging system.
Figure 2:
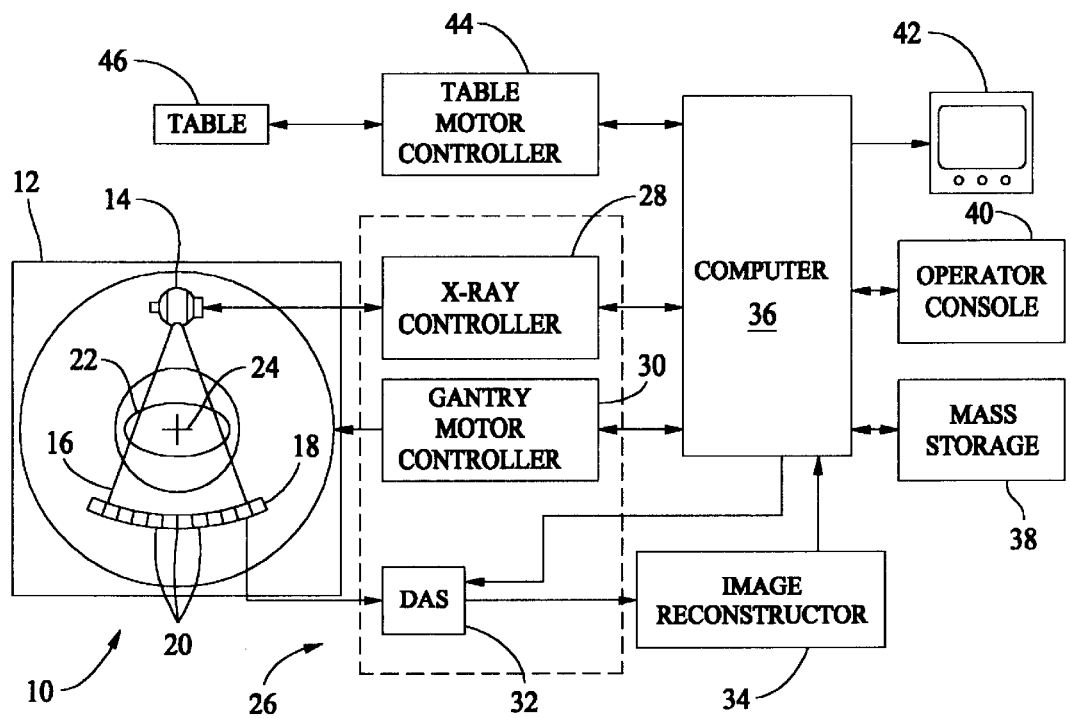
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam 16 is collimated by a collimator (not shown) to lie within an X-Y plane of a Cartesian coordinate system and generally referred to as an "imaging plane". Detector array 18 is formed by detector elements 20 which together sense the projected x-rays that pass through an object 22 such as a medical patient. Detector array 20 may be a single-slice detector or a multi-slice detector. Each detector element 20 produces an electrical signal that represents the intensity of an impinging x-ray beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 along a Z-axis through gantry opening 48.

Figure 3:
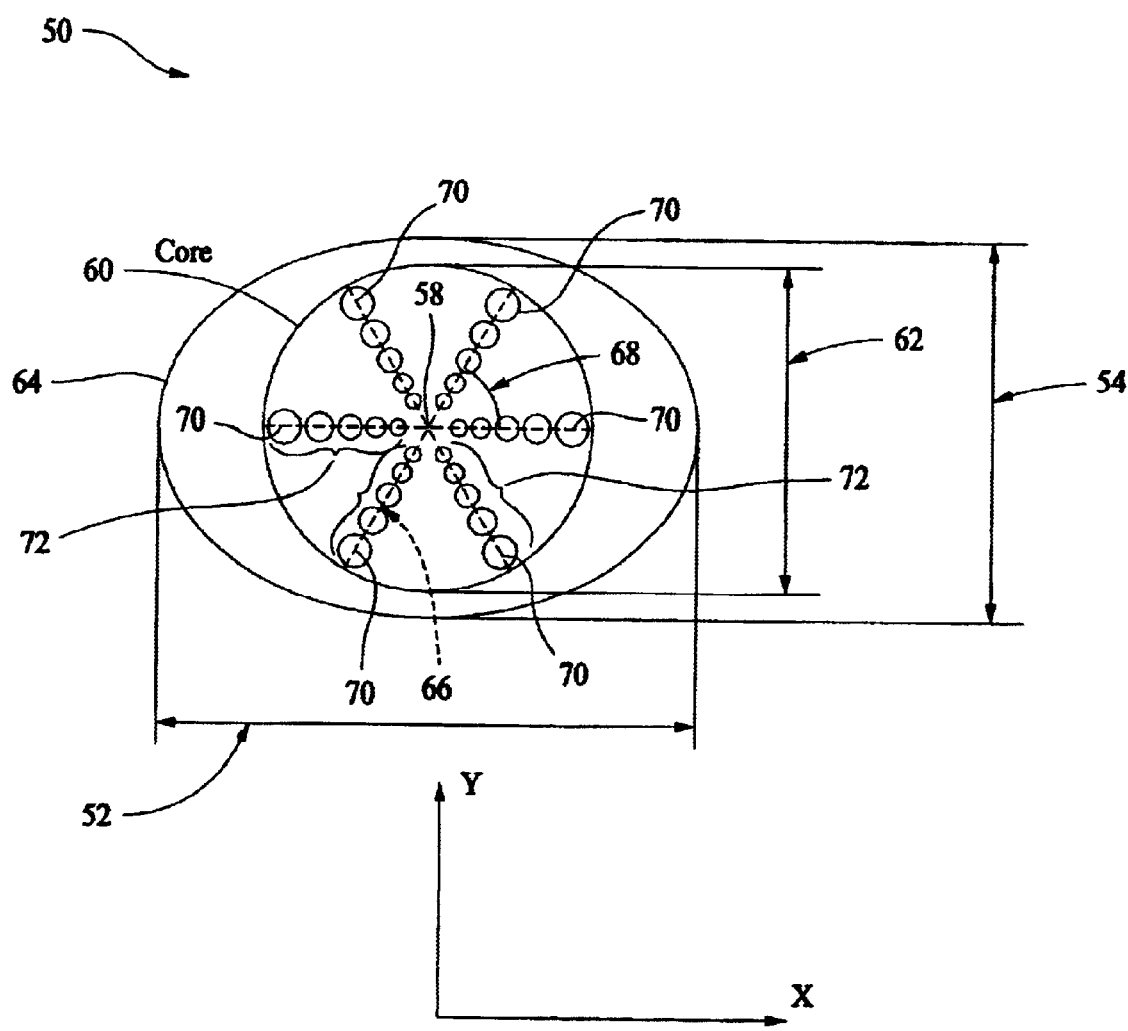
FIG. 3 is a frontal view of a phantom for calcium scoring.

In one embodiment and referring to FIG. 3, a phantom 50 for use in calcium scoring simulates regions of the human coronary system. As shown frontally in FIG. 3, e.g. in an X-Y plane, phantom 50 is oval in shape, having, for example, a long axis 52 of 35 centimeters and a short axis 54 of 25 centimeters. Phantom 50 includes a cylindrical core 60 representing the heart and having a diameter 62, for example, of 20 centimeters. Core 60 is made of a material having a CT number simulating that of heart muscle, for example, a plastic material having a CT number of 60 Hounsfield units at a source 14 voltage of 120 kilovolts.

Core 60 is located, e.g. centered, inside an elliptical ring 64 representing tissues surrounding the heart. Ring 64 is made of a material having a CT number simulating that of heart tissue, for example, a plastic material having a CT number of 60 Hounsfield units at a source 14 voltage of 120 kilovolts. As shall be described below, a plurality of rods (not shown in FIG. 3) are embedded in core 60 along lines 66 radiating from a phantom axis 58 (shown in FIG. 3 as coming out of the page, i.e. orthogonal to the X-Y plane shown in FIG. 3). Radial lines 66 extend at angles 68 from phantom axis 58.

Figure 4:
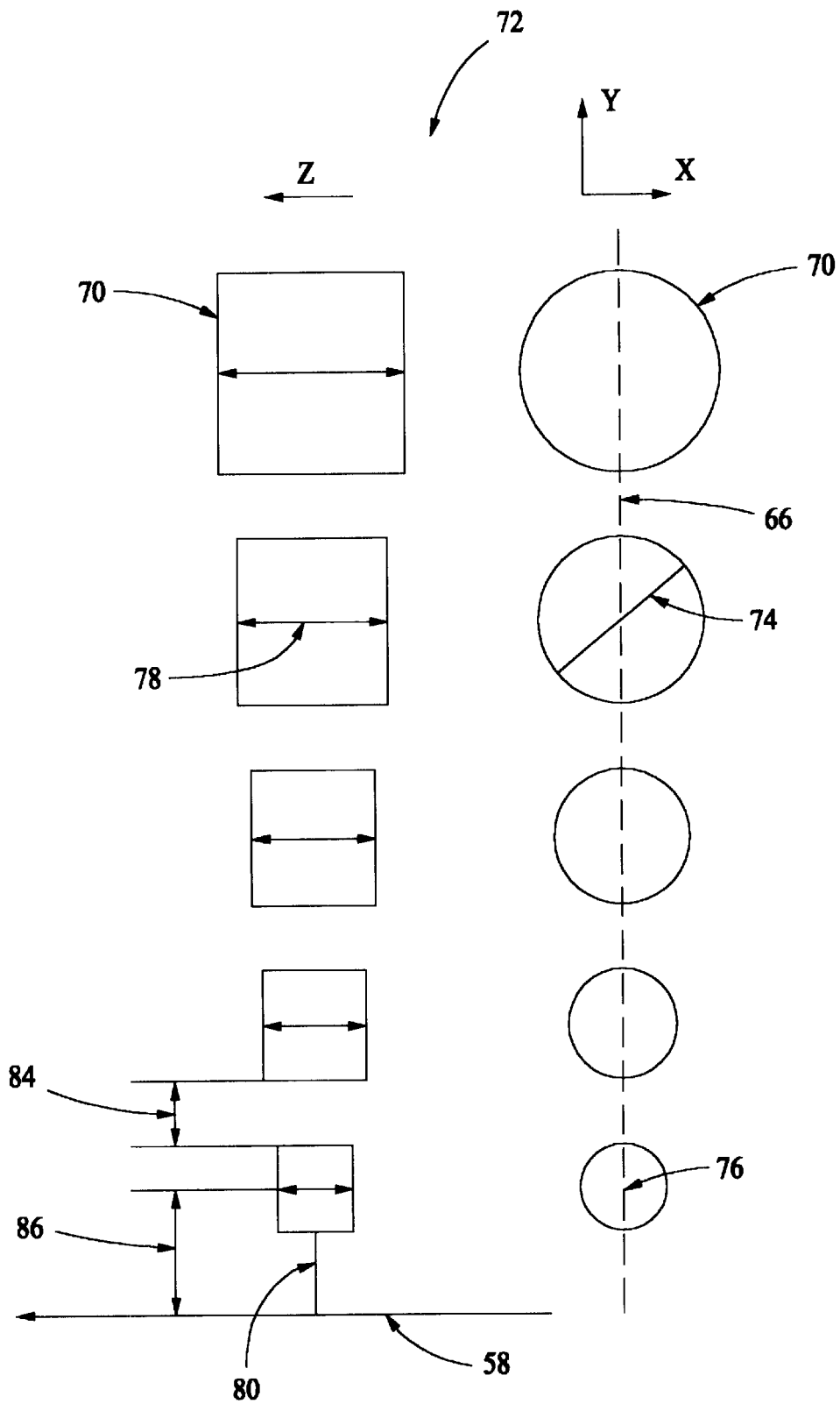
FIG. 4 is a diagram of shape and orientation for rods included in the phantom shown in FIG. 3.

As shown in FIG. 4, phantom 50 includes a plurality of volumes 70, e.g. rods, simulating a plurality of calcified coronary regions. Rods 70 differ from one another in length, diameter and density. Each rod 70 simulates, in dimensions and density, a calcified material typically found in patient coronary systems. More particularly and in one embodiment, thirty rods 70 are embedded in core 60 in six groups 72 of five rods 70 each. Each group 72 is arranged along a radial line 66 and has a target CT number (not shown in FIG. 4) as shall be described below. Rods 70 in each group 72 are separated from one another by a distance 84 of, for example, four millimeters and have diameters 74 of 2, 3, 4, 5 and 6 millimeters respectively, with diameters 74 increasing with distance from phantom axis 58. Center 76 of smallest rod 70 in a group 72 is located, for example, a distance 86 of five millimeters from phantom axis 58 along the appropriate radial line 66. Each rod 70 has, for example, a length 78 equal to its diameter 74 and is aligned lengthwise parallel to phantom axis 58. All rods 70 are lengthwise-centered on a midplane 80 which bisects phantom 50.

Figures 5, 6:
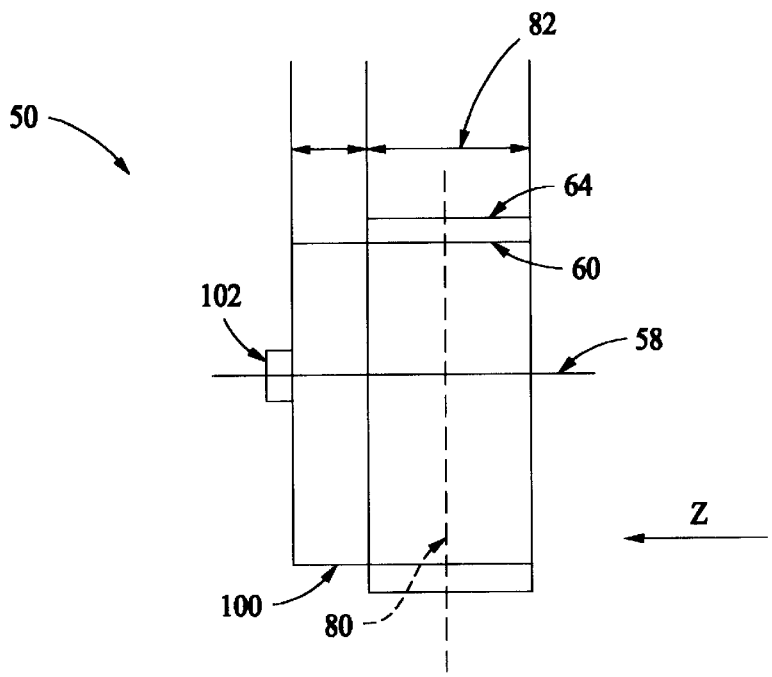
FIG. 5 is a table of CT number ranges and corresponding group target CT numbers and positional angles for one embodiment of the phantom shown in FIG. 3.
FIG. 6 is a side view of the phantom shown in FIG. 3.

Each group 72 is made of a material having a CT number representative of a range of calcium densities as reflected in CT images through the CT number. CT numbers (and materials having such numbers) are selected for rods 70 based on, for example, a scoring algorithm used by a calcium scoring system with which phantom 50 is to be used. One such algorithm categorizes calcification according to CT number in calcium density ranges 90 as shown in FIG. 5. For a 120-kilovolt source 14 voltage, ranges 90 include, for example, zero to 129 Hounsfield units, 130 to 199 Hounsfield units, 200 to 299 Hounsfield units, 300 to 399 Hounsfield units, and above and including 400 Hounsfield units. With one exception as shall be described below, a target CT number 92 is selected for each group 72 from the middle of the corresponding range 90. A middle value is selected to prevent range 90 boundary crossing when system 10 is subjected to noise. An exception is a calibration group 94 that is used to verify imaging system 10 accuracy. Calibration group 94 has a target CT number 92 of zero while other groups 72 have target CT numbers 92 of, e.g. 110, 150, 250, 350 and 450 Hounsfield units respectively. Phantom 50 is fabricated such that actual target CT numbers 92 are within tolerances of +5 HU and −5 HU of nominal target CT numbers 92. Thus nominal CT numbers are closely approximated without engendering fabrication difficulty. Groups 72 are positioned along radial lines 66, for example, at angles 68 as shown in FIG. 5, i.e. at 0 degrees, 45 degrees, 135 degrees, 180 degrees, 225 degrees, and 315 degrees respectively.

Figure 7:
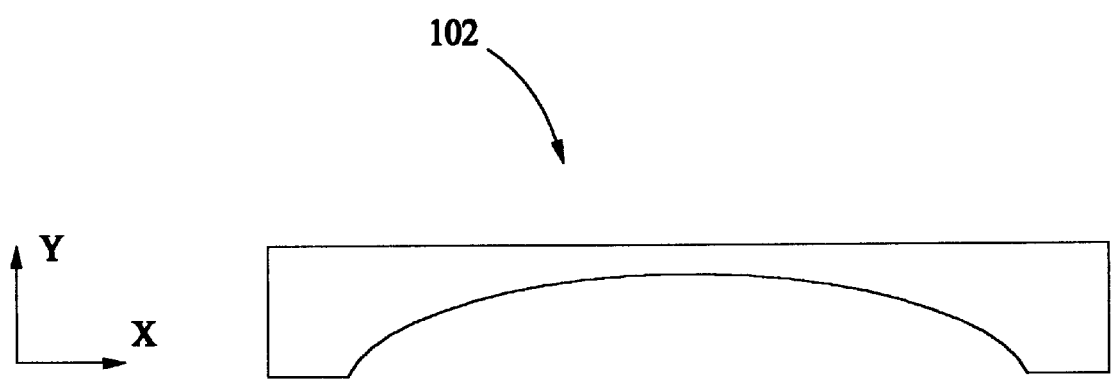
FIG. 7 is a diagram of a mounting bracket for the phantom shown in FIG. 3.

As shown in FIG. 6, core 60 and ring 64 are cylindrical in shape along phantom axis 58 and have a length 82 of, e.g., five centimeters. Core 60 has an alignment region 100 extending, for example, three centimeters in the direction of phantom axis 58. Phantom 50 includes a mounting bracket 102, removably affixed to alignment region 100 and shown frontally in FIG. 7. Phantom 50 is supported during imaging by a phantom holder (not shown), to which mounting bracket 102 is removably affixed.

In use, phantom 50 and the supporting phantom holder are placed on table 46. A centroid of phantom 50 is calculated and, based on the calculated centroid, phantom 50 is aligned by, for example, extending alignment region 100 up to three centimeters in the direction of the imaging system 10 Z-axis (along which table 46 is moved during imaging). Rods 70 are aligned along the imaging system 10 Z-axis.

When phantom 50 is placed on table 46 and aligned for imaging in imaging system 10, it simulates, for example, calcified coronary arterial regions of interest to the user of a calcium scoring system. The user then generates imaging system 10 images of the simulated calcified regions, calcium-scores the images, and compares results of the calcium scoring to expected phantom-image results.

The above-described phantom allows a user of a calcium scoring system to evaluate scoring system accuracy. The user also can evaluate different imaging systems (e.g. single-slice CT or multi-slice CT), different scanning methods (e.g. helical or axial), and different reconstruction algorithms relative to the calcium scoring system. and thereby determine whether a calcium score is valid, reproducible and repeatable.

Although an embodiment of phantom 50 is shown herein relative to a CT imaging system and for use with a calcium scoring system using a scoring algorithm, phantom 50 can also be used with other imaging systems, other calcium scoring systems and other scoring algorithms. Furthermore, phantom 50 is not limited to use with calcium scoring systems but can be used to quantify other substances besides calcium. Alternative embodiments of phantom 50 also can be used to evaluate patient regions of interest other than coronary arteries.

While the invention has been described in terms of various specific embodiments, those skilled in the art will recognize that the invention can be practiced with modification within the spirit and scope of the claims.

What is claimed is:

1. A method for evaluating substance scoring, the scoring based on imaging system-generated images of an object having regions of interest due to possible presence of the substance, said method comprising the steps of:

simulating the regions of interest using a phantom including a core, and a plurality of volumes comprising a plurality of rods embedded in the core, each volume simulating a region of interest;

generating images of the phantom;

substance scoring the generated images of the phantom; and comparing results of the substance scoring to expected phantom-image results.

2. A method in accordance with claim 1 wherein said step of simulating the regions of interest using a phantom comprises the steps of:

providing a phantom including a plurality of volumes, each volume having dimensions simulating a region of interest, each volume having a target CT number representative of a density of the substance; and aligning the phantom with the imaging system.

3. A method in accordance with claim 2 wherein the imaging system includes a table, and said step of aligning the phantom with the imaging system comprises the steps of:

calculating a centroid of the phantom; and locating the phantom on the table based on the calculated centroid.

4. A method in accordance with claim 2 wherein the plurality of volumes include a plurality of rods and said step of aligning the phantom with the imaging system comprises the step of aligning the rods relative to a Z-axis of the imaging system.

5. A phantom for evaluating substance scoring, the scoring based on images of an object having regions of interest due to possible presence of the substance, said phantom comprising:

a core, wherein said core comprises a CT number representative of heart of heart muscle density;

a ring surrounding said core, wherein said ring comprises a CT number representative of density of tissue surrounding a heart; and a plurality of volumes comprising a plurality of rods embedded in said core, each said volume simulating a region of interest.

6. A phantom for evaluating substance scoring, the scoring based on images of an object having regions of interest due to possible presence of the substance, said phantom comprising:

a core;

a plurality of volumes comprising a plurality of rods embedded in said core, each said volume simulating a region of interest and each said volume comprises a target CT number representative of a density of the substance within the region of interest simulated by said volume; and a substance scoring to be evaluated using a scoring algorithm and each said target CT number reflects a substance density range utilized by the scoring algorithm, wherein the substance being scored is calcium and said target CT numbers reflect substance density ranges of zero to 129 Hounsfield unites, 130 to 199 Hounsfield unites, 200 to 299 Hounsfield units, 300 to 399 Hounsfield unites, and greater than or equal to 400 Hounsfield units.

7. A phantom in accordance with claim 6 wherein said target CT numbers are configured to avoid substance density range boundary crossing.

8. A phantom in accordance with claim 7 wherein said target CT numbers comprise 110 Hounsfield units, 150 Hounsfield units, 250 Hounsfield units, 350 Hounsfield units, and 450 Hounsfield units.

9. A phantom for evaluating substance scoring, the scoring based on images of an object having regions of interest due to possible presence of the substance, said phantom comprising:

a core;

a plurality of volumes comprising a plurality of rods embedded in said core, each said volume simulating a region of interest; and a phantom axis around which said rods are embedded in a plurality of radial lines, wherein said radial lines extend from said phantom axis at angles of zero degrees, 45 degrees, 135 degrees, 180 degrees, 225 degrees, and 315 degrees.

10. A phantom in accordance with claim 9 wherein each said volume comprises dimensions simulating dimensions of a region of interest.

11. A phantom in accordance with claim 9 wherein at least one said volume comprises a target CT number of zero.

12. A phantom in accordance with claim 9 further comprising a midplane bisecting said phantom, said rods being lengthwise-centered on said midplane.

13. A phantom for evaluating substance scoring, the scoring based on images of an object having regions of interest due to possible presence of the substance, said phantom comprising:

a core;

a phantom axis and an alignment region adjacent to said core, the alignment region extending from said core in a phantom-axis direction; and a plurality of volumes comprising a plurality of rods embedded in said core, each said volume simulating a region of interest.

14. A phantom in accordance with claim 13 further comprising a mounting bracket connected to said alignment region and removably affixed to a phantom holder.

* * * * *